(12) United States Patent
Van Hal et al.

(10) Patent No.: US 7,517,344 B2
(45) Date of Patent: Apr. 14, 2009

(54) DEVICE FOR TREATING HUMAN SKIN BY MEANS OF RADIATION

(75) Inventors: Robbert Adrianus Maria Van Hal, Eindhoven (NL); Bernardus Leonardus Gerardus Bakker, Eindhoven (NL); Paul Anton Josef Ackermans, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 255 days.

(21) Appl. No.: 10/536,242

(22) PCT Filed: Oct. 31, 2003

(86) PCT No.: PCT/IB03/04961

§ 371 (c)(1),
(2), (4) Date: May 24, 2005

(87) PCT Pub. No.: WO2004/047921

PCT Pub. Date: Jun. 10, 2004

(65) Prior Publication Data

US 2006/0015091 A1 Jan. 19, 2006

(30) Foreign Application Priority Data

Nov. 28, 2002 (EP) .................................. 02079976

(51) Int. Cl.
*A61B 18/18* (2006.01)
(52) U.S. Cl. ................................. 606/9; 606/10; 607/88
(58) Field of Classification Search ............... 606/8–10, 606/23, 25; 607/88–91; 359/885–892
See application file for complete search history.

(56) References Cited

U.S. PATENT DOCUMENTS

| 3,753,822 | A | * | 8/1973 | Heinrich | ..................... 156/101 |
| 4,805,989 | A | * | 2/1989 | Nakajima | ................... 359/584 |
| 5,425,754 | A | * | 6/1995 | Braun et al. | .................. 607/88 |

(Continued)

FOREIGN PATENT DOCUMENTS

EP 0885629 A 12/1996

(Continued)

*Primary Examiner*—Ahmed M Farah

(57) ABSTRACT

The invention relates to a device (1) for treating human skin by means of radiation. The device comprises a housing (3) with a radiation exit opening (13). A radiation source (9) is accommodated in the housing. Radiation generated by the radiation source propagates from the radiation source towards the radiation exit opening via a radiation path (15) comprising a radiation filter having a predetermined transmission spectrum. According to the invention the radiation filter comprises a reflecting surface (23) via which the radiation propagating along the radiation path (15) is reflected. The reflecting surface has a coating which provides the reflecting surface with a reflection spectrum substantially matching the predetermined transmission spectrum. An advantage is that the reflection surface can be optimally and uniformly cooled, so that the heat generated as a result of the absorption of part of the radiation by the radiation filter can be effectively transmitted to a cooling system (25) of the device (1). In a particular embodiment the device (1) is an epilator for removing hairs from the human skin and the radiation source (9) is a flash lamp. The radiation path (15) is enclosed by a channel (17) having a bend (19) and having an inner wall (21) on which the reflecting surface (23) is provided.

13 Claims, 3 Drawing Sheets

U.S. PATENT DOCUMENTS

Figure 1:
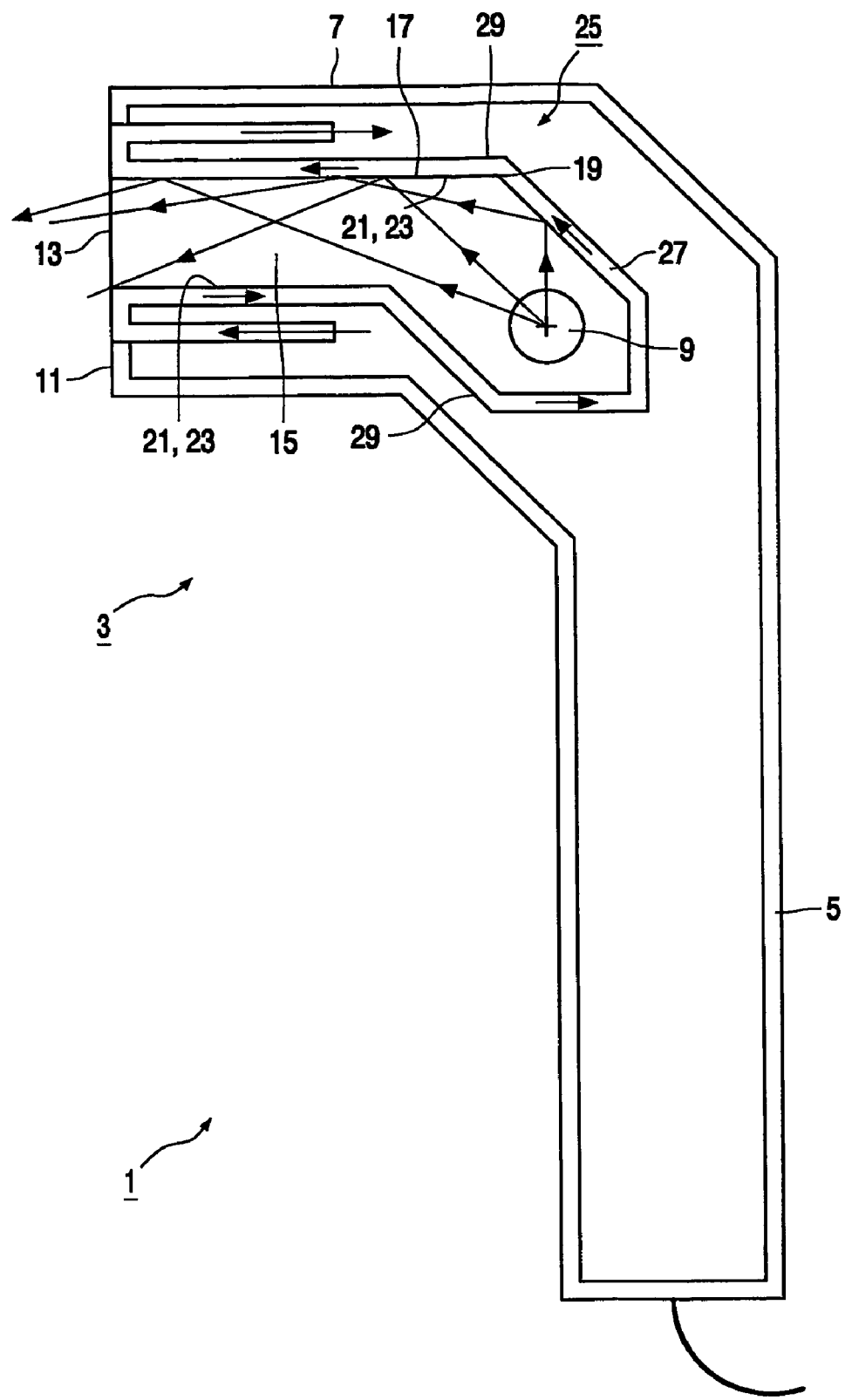

| | | | |
|---|---|---|---|
| 5,735,844 A * | 4/1998 | Anderson et al. | 606/9 |
| 5,755,751 A * | 5/1998 | Eckhouse | 607/88 |
| 5,830,208 A * | 11/1998 | Muller | 606/9 |
| 5,867,329 A * | 2/1999 | Justus et al. | 359/861 |
| 5,961,543 A * | 10/1999 | Waldmann | 607/88 |
| 6,228,074 B1 * | 5/2001 | Almeida | 606/9 |
| 6,261,310 B1 * | 7/2001 | Neuberger et al. | 607/89 |
| 6,280,438 B1 | 8/2001 | Eckhouse et al. | |
| 6,514,243 B1 * | 2/2003 | Eckhouse et al. | 606/9 |
| 7,083,610 B1 * | 8/2006 | Murray et al. | 606/9 |
| 7,097,639 B1 * | 8/2006 | Almeida | 606/9 |
| 7,147,654 B2 * | 12/2006 | Baumgardner et al. | 607/88 |
| 7,252,628 B2 * | 8/2007 | Van Hal et al. | 600/1 |
| 7,268,940 B2 * | 9/2007 | Veith et al. | 359/388 |
| 2002/0173780 A1 * | 11/2002 | Altshuler et al. | 606/9 |

FOREIGN PATENT DOCUMENTS

| | | |
|---|---|---|
| EP | 0775504 A | 5/1997 |
| EP | 0775504 A2 | 5/1997 |
| EP | 0885629 A2 | 12/1998 |
| GB | 2360946 A | 10/2001 |
| WO | 0187408 A | 11/2001 |
| WO | WO 0187408 A2 | 11/2001 |

* cited by examiner

DEVICE FOR TREATING HUMAN SKIN BY MEANS OF RADIATION

The invention relates to a device for treating human skin by means of radiation, which device comprises a housing with a radiation exit opening, a radiation source accommodated in the housing, and a radiation path between the radiation source and the radiation exit opening, said radiation path comprising a radiation filter having a predetermined transmission spectrum.

A device for treating human skin of the kind mentioned in the opening paragraph is known from U.S. Pat. No. 6,280,438 B1. The known device is used to remove hairs from human skin by means of light pulses having a relatively high energy density. The radiation source is a gas-filled linear flash lamp which is arranged in the focus of an elliptical reflector and generates pulsed light having a relatively broad spectrum. The radiation filter is a plate-shaped filter which is arranged in the radiation path transversely to a main direction of the radiation path and covers the radiation exit opening, so that the light generated by the flash lamp passes through the filter. The transmission spectrum of the radiation filter is such that the filter transmits the portion of the spectrum of the generated light which is effective for the removal of the hairs and which has no unwanted side effects on the skin, and absorbs the portion of the spectrum of the generated light which would have unwanted side effects on the skin. In this manner the hairs are removed in an effective manner, while side effects on the skin, such as burns, are prevented as much as possible.

As a result of the absorption by the radiation filter of said portion of the spectrum of the generated light, the filter is heated. Since the generated light pulses have a relatively high energy density, a relatively large amount of energy is absorbed by the radiation filter. A disadvantage of the known device for treating human skin is that the radiation filter is cooled only to a limited extent, because only a circumferential portion of the filter is in direct thermal contact with the housing of the device. As a result, during operation excessive thermal deformations of the filter occur, which can lead to permanent deformations or even fracture of the filter.

It is an object of the invention to provide a device for treating human skin as mentioned in the opening paragraph having a radiation filter which can be better cooled, so that the risk of permanent deformations or fracture of the filter is limited.

In order to achieve this object, a device for treating human skin in accordance with the invention is characterized in that the radiation filter comprises a reflecting surface via which the radiation propagating along the radiation path is reflected and which has a coating providing the reflecting surface with a reflection spectrum substantially matching the predetermined transmission spectrum. In the device for treating human skin in accordance with the invention the radiation generated by the radiation source is filtered as a result of the predetermined reflecting properties of said reflecting surface. A portion of the spectrum of the generated radiation, which is effective for the intended treatment of the human skin and which has no unwanted side effects on the skin, is reflected by said reflecting surface, while a portion of the spectrum of the generated radiation, which would have unwanted side effects on the skin, is absorbed by said reflecting surface. The reflecting surface is arranged adjacent the radiation path and bounds the radiation path in such a manner that at least a substantial portion of the radiation is reflected once or, preferably, more than once by the reflecting surface while propagating from the radiation source towards the radiation exit opening. The reflecting surface does not need to be transparent to the radiation. As a result all portions of the reflecting surface can be brought into direct thermal contact with a cooling system of the device, so that an improved uniform thermal contact is achieved between the reflecting surface and the cooling system of the device. In this manner, thermal deformations of the reflecting surface are limited and local excessive thermal deformations of the reflecting surface are even prevented, so that permanent deformations and fracture of the radiation filter are prevented.

A particular embodiment of a device for treating human skin in accordance with the invention is characterized in that the radiation filter comprises a channel which encloses the radiation path and which comprises an inner wall on which the reflecting surface is provided. In this embodiment the radiation propagates from the radiation source towards the radiation exit opening through said channel. Since the reflecting surface is provided on the inner wall of said channel, the radiation propagating through the channel will be reflected by the reflecting surface. In this manner the radiation filter is very effective, and the filter has a practical structure.

A further embodiment of a device for treating human skin in accordance with the invention is characterized in that the channel comprises a bend situated between the radiation source and the radiation exit opening. As a result of the presence of said bend in the channel, all portions of the radiation propagating through the channel are forced to strike the inner wall of the channel on which the reflecting surface is provided. As a result, all portions of the radiation propagating through the channel are reflected by the reflecting surface once or even more than once, so that the effectiveness of the filter is further improved.

A particular embodiment of a device for treating human skin in accordance with the invention is characterized in that the reflecting surface comprises a first portion, which has a first coating material providing said first portion with a first reflection spectrum, and a second portion, which has a second coating material providing said second portion with a second reflection spectrum, said first and said second reflection spectrum together matching the predetermined transmission spectrum. For most treatments of the human skin, such as the removal of hairs from the human skin, the predetermined transmission spectrum of the radiation filter should be such that a first portion of the radiation having wavelengths below a first limit are absorbed by the filter, that a second portion of the radiation having wavelengths between said first limit and a second limit above said first limit is transmitted by the filter, and that a third portion of the radiation having wavelengths above said second limit is absorbed by the filter. In this particular embodiment such a profile of the transmission spectrum is achieved in a practical manner if the first reflection spectrum is such that the first portion of the reflecting surface substantially completely absorbs radiation having wavelengths below said first limit and substantially completely reflects radiation having wavelengths above said first limit, and if the second reflection spectrum is such that the second portion of the reflecting surface substantially completely reflects radiation having wavelengths below said second limit and substantially completely absorbs radiation having wavelengths above said second limit.

A particular embodiment of a device for treating human skin in accordance with the invention is characterized in that the reflecting surface is provided on a wall which is in thermal contact with a cooling system. A uniform thermal contact is present between the reflecting surface and said wall. The cooling system can be designed in such a manner that a uniform thermal contact is also present between said wall and said cooling system. In this manner, a simple and practical structure is achieved to uniformly cool the reflecting surface.

A further embodiment of a device for treating human skin in accordance with the invention is characterized in that the cooling system comprises a circuit filled with a cooling fluid, the wall being in thermal contact with said circuit. As a result of the use of said circuit, the wall and the reflecting surface provided thereon are uniformly cooled.

A further embodiment of a device for treating human skin in accordance with the invention is characterized in that the cooling system comprises a fan for generating a gas stream and a guide for guiding said gas stream along the wall. As a result of the use of said fan and said guide, the wall and the reflecting surface provided thereon are uniformly cooled.

A particular embodiment of a device for treating human skin in accordance with the invention is characterized in that the device is a device for removing hairs from human skin, wherein the radiation source is a flash lamp. The light of the flash lamp has a relatively broad spectrum ranging from UV light to near IR light. The portion of this spectrum, which is effective for the removal of hairs from human skin, lies between approximately 600 nm and 900 nm. The portions of this spectrum below approximately 600 nm and above approximately 900 nm are not effective for the removal of hairs and in addition cause unwanted side effects on the skin such as burns or even DNA mutations. The energy density of the light necessary to remove the hairs is relatively high, so that the radiation filter has to absorb a large amount of energy. In view of these properties of the light of the flash lamp, the invention is particularly suitable for use in a device for removing hairs by means of a flash lamp.

Figure 2:
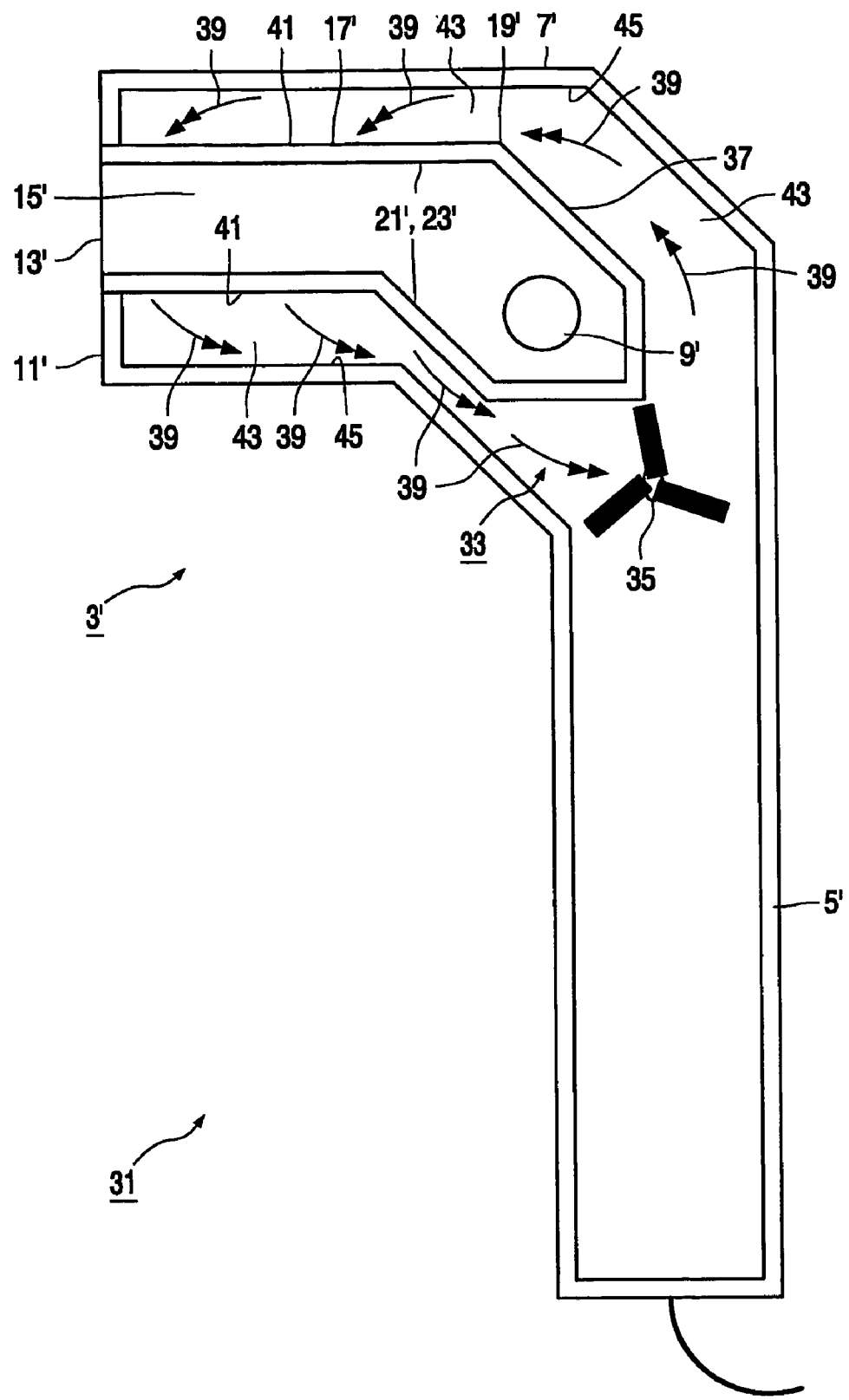
Figure 3:
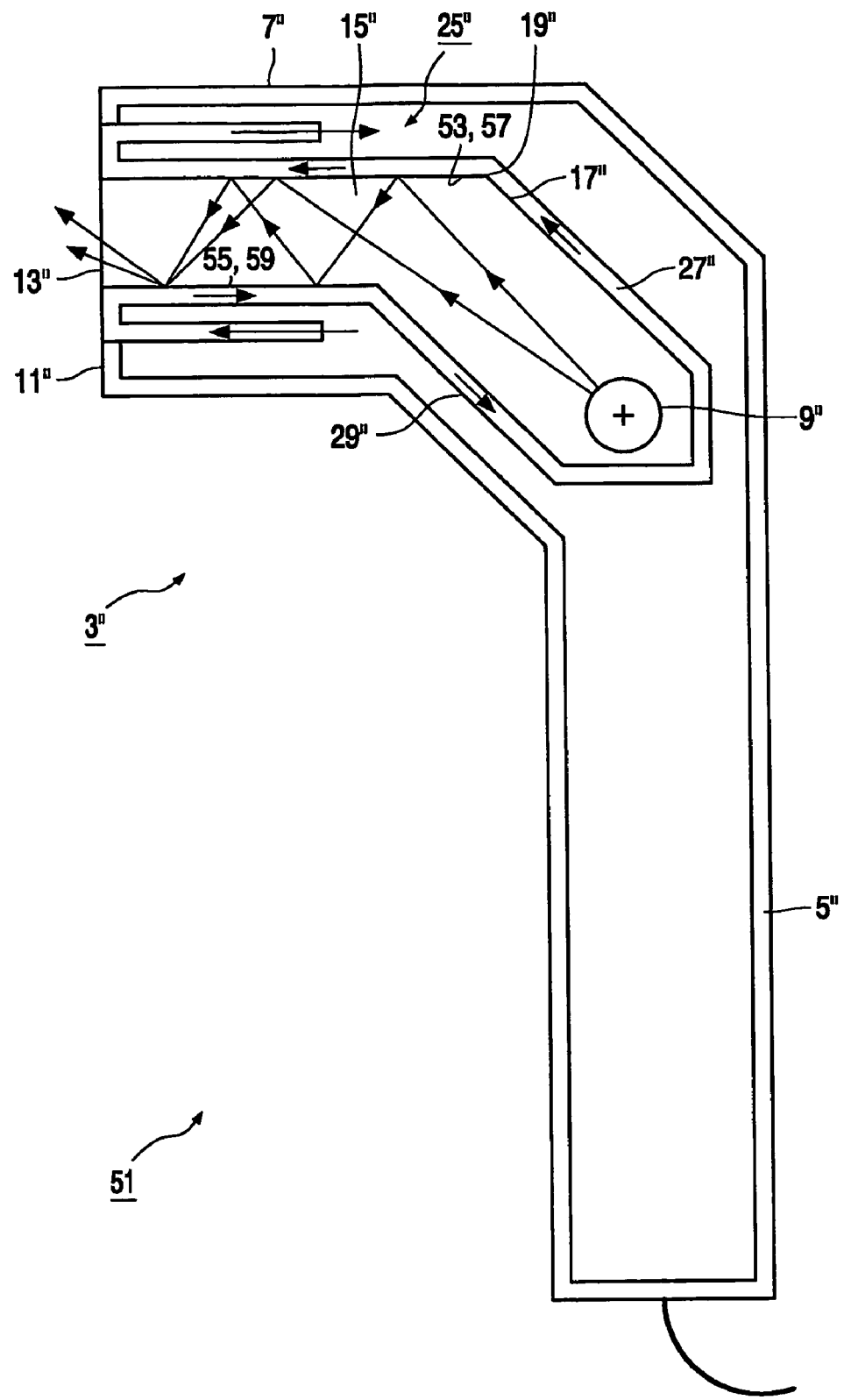

Embodiments of a device for treating human skin by means of radiation according to the invention will be described hereafter with reference to the figures, in which FIG. 1 schematically shows a first embodiment of a device for treating human skin in accordance with the invention, FIG. 2 schematically shows a second embodiment of a device for treating human skin in accordance with the invention, and FIG. 3 schematically shows a third embodiment of a device for treating human skin in accordance with the invention.

The first embodiment of a device 1 for treating human skin is a device for removing hairs from human skin, in particular an epilator for removing the hairs for a relatively long time or even permanently. FIG. 1 schematically shows only the main parts of the device 1 which are necessary to understand the principles of the invention. The device 1 comprises a housing 3 having a grip 5 and a head 7 mounted on the grip 5. The head 7 accommodates a radiation source 9, which is a gas-filled linear flash lamp in this particular embodiment. In a front portion 11 of the head 7 a radiation exit opening 13 is provided for the light generated during operation by the radiation source 9. The head 7 further accommodates a radiation path 15, which extends between the radiation source 9 and the radiation exit opening 13. During operation the radiation source 9 generates light pulses having a relatively high energy density, which propagate from the radiation source 9 towards the radiation exit opening 13 and irradiate the human skin present in front of the radiation exit opening 13. Part of the light is absorbed by the hair roots and the hair follicles present in the skin, which are considerably heated as a result of the relatively high energy density of the light. As a result the hair roots and the hair follicles are damaged or even destroyed, so that growing of the hairs is prevented for a considerably long time or even permanently.

In the embodiment shown in FIG. 1 the radiation path 15 is enclosed by a channel 17 having a rectangular or square cross section and having a bend 19 situated between the radiation source 9 and the radiation exit opening 13. An inner wall 21 of the channel 17 is provided with a reflecting surface 23. As a result of the presence of the bend 19 all portions of the light propagating from the radiation source 9 towards the radiation exit opening 13 are forced to strike the inner wall 21 and to be reflected at least once by the reflecting surface 23 provided on the inner wall 21. The reflecting surface 23 has a coating which provides the reflecting surface 23 with a predetermined reflection spectrum. In the embodiment shown in FIG. 1 said coating is a highly reflective dielectric multilayer mirror coating (Suffix: 503) sold by JML Optical Industries and disclosed on page G-18 of the brochure JML Direct Optics, third edition. This particular coating has a relatively low reflection coefficient for wavelengths below approximately 600 nm and above approximately 900 nm. For wavelengths between approximately 680 nm and 850 nm this particular coating has a reflection coefficient of approximately 100%. Because the radiation source 9 has a relatively broad spectrum ranging from UV light to near IR light, the channel 17 comprising the reflecting surface 23 does not only define and bound the radiation path 15, but is also effectively used as a radiation filter of the radiation path 15 having a predetermined transmission spectrum, wherein the reflection spectrum of the reflecting surface 23 substantially matches said predetermined transmission spectrum. In the embodiment of FIG. 1 the radiation filter thus substantially completely transmits the portions of the light from the radiation source 9 having wavelengths between approximately 680 nm and 850 nm. These portions of the wavelengths are particularly effective for the removal of hairs from human skin without causing inadmissible side effects on the skin. The radiation filter absorbs a major portion of the light from the radiation source 9 having wavelengths below approximately 600 nm and above approximately 900 nm. These portions of the wavelengths are not effective for the removal of hairs and would only cause unwanted side effects on the skin such as burns or even DNA mutations. In this manner the hairs are effectively removed by the light from the radiation source 9, but unwanted side effects of the light on the human skin are prevented as much as possible by the presence of the radiation filter.

The portions of the spectrum of the light from the radiation source 9, which are not reflected by the reflecting surface 23, are absorbed by the inner wall 21, which is made from a light absorbing material such as black glass. As a result, the inner wall 21 is heated. Since the light pulses generated by the radiation source 9 have a relatively high energy density, a relatively large amount of energy is absorbed by the inner wall 21. An advantage of the use of the reflecting surface 23 as the radiation filter for the generated light is that the reflecting surface 23 does not need to be transparent to the radiation in view of its position adjacent the radiation path 15. As a result all portions of the reflecting surface 23 can be brought into direct thermal contact with a cooling system 25 of the device 1. In the embodiment shown in FIG. 1 the cooling system 25 comprises a circuit 27 filled with a cooling fluid. The circuit 27 is bounded by the inner wall 21 of the channel 23 and by an additional wall 29 arranged parallel to the inner wall 21. The device 1 further comprises pumping means not shown in FIG. 1 for pumping the cooling fluid through the circuit 27 and along the inner wall 21. Thus all portions of the inner wall 21 are in direct thermal contact with the circuit 27 of the cooling system 25. As a result a uniform thermal contact is provided between the inner wall 21 and the cooling system 25. Since the inner wall 21 is thus uniformly cooled by the cooling system 25, thermal deformations of the reflecting surface 23 are limited and local excessive thermal deformations of the reflecting surface 23 are even prevented, so that permanent deformations and damage or fracture of the radiation filter are prevented.

It is noted that the position of the reflecting surface 23 relative to the radiation path 15 should be such that at least a major portion of the light generated by the radiation source 9 is reflected once by the reflecting surface 23. Preferably all portions of the generated light are reflected by the reflecting surface 23, and preferably more than once. It will be understood that a person skilled in the art of optics will be able to establish in a straightforward manner the geometry and dimensions of the channel 17 and the reflecting surface 23 in such a manner that this condition is met. It is noted that the presence of the bend 19 increases the amount of light being reflected by the reflecting surface 23, so that the effectiveness of the radiation filter is considerably improved. However, the presence of said bend 19 is not essential, and sufficient reflecting properties can also be obtained for example by means of a straight channel having a relatively large ratio between its length and width. Further, the invention also includes embodiments in which the radiation filter comprises more than one channel or a plurality of channels, for example a matrix of channels, provided with reflecting surfaces on their inner walls. It is further noted that the effectiveness of the radiation filter of the device 1 is increased as a result of the use of the channel 17, and that in this manner the radiation filter has a practical structure. It is noted, however, that the use of the channel 17 or of light guiding channels in general is not essential. The reflecting surface may, for example, also be provided on a single wall structure, or on a series of adjacent or consecutive wall structures, which are in such a position relative to the radiation path that a substantial portion of the light generated by the radiation source 9 is reflected by the reflecting surface before passing the radiation exit opening.

The second embodiment of a device 31 for treating human skin in accordance with the invention also is a device for removing hairs from human skin, in particular an epilator for removing the hairs for a relatively long time or even permanently. FIG. 2 schematically shows only the main parts of the device 31 which are necessary to understand the principles of the invention. Parts of the device 31 which correspond to parts of the device 1 shown in FIG. 1 and which were discussed in the foregoing are indicated by means of corresponding reference numbers in FIG. 2 and will not be discussed in detail. Hereafter only the main differences between the device 31 and the device 1 will be briefly discussed.

The device 31 mainly differs from the device 1 in that the device 31 comprises a cooling system 33 which is different from the cooling system 25 of the device 1. The cooling system 33 comprises a fan 35 which can be driven by an electric motor not shown in FIG. 2. The channel 17' is formed by a sheet 37 made from a light absorbing material on which the inner wall 21' having the reflecting surface 23' is provided. During operation the fan 35 generates an air stream 39, which is guided along a major portion of an outer surface 41 of the sheet 37 by means of guiding channels 43 provided between the sheet 37 and an inner wall 45 of the head 7'. As the air stream 39 is thus present along a major portion of the outer surface 41 of the sheet 37, also in this second embodiment a substantially uniform cooling of the inner wall 21' is obtained. The cooling system 33 has a relatively simple and practical structure.

The third embodiment of a device 51 for treating human skin in accordance with the invention also is a device for removing hairs from human skin, in particular an epilator for removing the hairs for a relatively long time or even permanently. FIG. 3 schematically shows only the main parts of the device 51 which are necessary to understand the principles of the invention. Parts of the device 51 which correspond to parts of the device 1 shown in FIG. 1 and which were discussed in the foregoing are indicated by means of corresponding reference numbers in FIG. 3 and will not be discussed in detail. Hereafter only the main differences between the device 51 and the device 1 will be briefly discussed.

The device 51 mainly differs from the device 1 in that the geometry and the dimensions of the channel 17" of the device 51 and the position of the radiation source 9" are such that all portions of the light generated by the radiation source 9" are reflected at least twice by the inner walls of the channel 17", i.e. at least once by an upper inner wall 53 of the channel 17" and at least once by a lower inner wall 55 of the channel 17". This reflecting property of the channel 17" is mainly achieved by means of a relatively large ratio between the length and the width of the channel 17", but it will be understood that a person skilled in the art of optics will be able to establish in a straightforward manner more exact values of the main dimensions of the channel 17" by means of which said reflecting property can be achieved. Said upper inner wall 53 comprises a first portion 57 of a reflecting surface of the channel 17", while said lower inner wall 55 comprises a second portion 59 of said reflecting surface. Said first portion 57 and said second portion 59 of the reflecting surface are provided with respectively a first coating material and a second coating material, said first coating material providing said first portion 57 with a first reflection spectrum and said second coating material providing said second portion 59 with a second reflection spectrum. In the embodiment shown in FIG. 3 said first coating material is a coating material as specified in the Linos Photonics catalog, 2001, section thin film coatings, page H13, item FKP-5. This coating material has a so-called edge wavelength of approximately 600 nm, so that the first coating material has a relatively low reflection coefficient for wavelengths below approximately 600 nm and a relatively high reflection coefficient for wavelengths above approximately 600 nm. In the embodiment shown in FIG. 3 said second coating material is a coating material as specified in the Linos Photonics catalog, 2001, section thin film coatings, page H14, item FLP-5. This coating has an edge wavelength of approximately 900 nm, so that the second coating material has a relatively high reflection coefficient for wavelengths below approximately 900 nm and a relatively low reflection coefficient for wavelengths above approximately 900 nm. Since all portions of the light generated by the radiation source 9" are reflected at least once by the upper inner wall 53 and at least once by the lower inner wall 55, a major portion of the light having wavelengths below approximately 600 nm will be absorbed by said first portion 57 of the reflecting surface, a major portion of the light having wavelengths above approximately 900 nm will be absorbed by said second portion 59 of the reflecting surface, and a major portion of the light having wavelengths between approximately 600 nm and 900 nm will be reflected by both said first and said second portion 57, 59 of the reflecting surface and will consequently be transmitted by the radiation filter of the device 51. Thus said first and said second reflection spectrum of, respectively, said first and said second portion 57, 59 of the reflecting surface together match a predetermined transmission spectrum of the radiation filter of the device 51 which roughly corresponds with the transmission spectrum of the radiation filter of the device 1.

The embodiments of a device 1, 31, 51 for treating human skin in accordance with the invention shown in FIGS. 1, 2, 3 and described hereinbefore are devices for removing hairs from human skin, in particular epilators for removing the hairs for a relatively long time or even permanently. It is noted, however, that the invention also includes other types of devices for treating human skin by means of radiation. Examples of such devices are devices for the medical or cosmetic treatment by means of radiation or radiation pulses of birthmarks present on the skin, such as naevus vinosus and naevus pigmentosus, psoriasis, or aberrations of blood vessels present in the skin, such as varicose veins. It will be understood that a person skilled in the art of such treatments of the human skin knows or will be able to establish which kind of radiation, and in particular which wavelengths of the radiation, is most effective for a particular kind of treatment and which wavelengths are not effective and harmful to the remaining part of the skin. On the basis of this information a person skilled in the art of optics will be able to establish in a straightforward manner the predetermined transmission spectrum of the radiation filter and to find a suitable coating or combination of coatings providing a reflection spectrum which matches said predetermined transmission spectrum.

It is further noted that in the description and the claims the expression "reflecting surface" is to be read in its proper context. A person skilled in the art will understand that, if reference is made to the portion of the light reflected by the reflecting surface, it is the coating that actually reflects said portion of the light. A person skilled in the art will also understand that, if reference is made to the portion of the light absorbed by the reflecting surface, the coating transmits said portion of the light and said portion of the light is actually absorbed by, for example, the wall, substrate or other structure on which the coating is provided. The invention also covers embodiments in which said portion of the light is directly absorbed by the cooling fluid of a cooling system. In such an embodiment, for example, the coating is provided on a light transmitting substrate, such as transparent glass, along which the cooling fluid flows.

In the embodiments shown in FIGS. 1, 2 and 3 the radiation paths 15, 15', 15" are air or gas-filled. It is finally noted that the invention also encloses embodiments in which the radiation path is filled with a fluid or in which the radiation path is even solid. Thus, for example, the radiation path may comprise a glass body through which the radiation propagates, the surface of the glass body being provided with a coating providing the surface of the glass body with the desired reflection spectrum for the radiation.

The invention claimed is:

1. A device for treating human skin through the use of radiation, which device comprises a housing with a radiation exit opening, a radiation source accommodated in the housing, and a radiation path between the radiation source and the radiation exit opening, said radiation path comprising a radiation filter having a predetermined transmission spectrum, wherein the radiation filter comprises a reflecting surface via which the radiation propagating along the radiation path is reflected and which has a coating providing the reflecting surface with a reflection spectrum substantially matching the predetermined transmission spectrum, wherein the radiation filter comprises a channel which encloses the radiation path and which comprises an inner wall on which the reflecting surface is provided, and wherein the channel comprises a bend situated between the radiation source and the radiation exit opening.

2. The device as claimed in claim 1, wherein the reflecting surface comprises a first portion, which has a first coating material providing said first portion with a first reflection spectrum, and a second portion, which has a second coating material providing said second portion with a second reflection spectrum, said first and said second reflection spectrum together matching the predetermined transmission spectrum.

3. The device as claimed in claim 1, wherein the reflecting surface is provided on a wall which is in thermal contact with a cooling system.

4. The device as claimed in claim 3, wherein the cooling system comprises a circuit filled with a cooling fluid, the wall being in thermal contact with said circuit.

5. The device as claimed in claim 3, wherein the cooling system comprises a fan for generating a gas stream and a guide for guiding said gas stream along the wall.

6. The device as claimed in claim 1, wherein the device is a device for removing hairs from human skin, wherein the radiation source is a flash lamp.

7. A device for treating human skin through the use of radiation, which device comprises a housing with a radiation exit opening, a radiation source accommodated in the housing, and a radiation path between the radiation source and the radiation exit opening, said radiation path comprising a radiation filter having a predetermined transmission spectrum, wherein the radiation if filter comprises a reflecting surface via which the radiation propagating along the radiation path is reflected and which has a coating providing the reflecting surface with a reflection spectrum substantially matching the predetermined transmission spectrum, wherein the reflecting surface comprises a first portion, which has a first coating material providing said first portion with a first reflection spectrum, and a second portion, which has a second coating material providing said second portion with a second reflection spectrum, said first and said second reflection spectrum together matching the predetermined transmission spectrum.

8. The device as claimed in claim 7, wherein the radiation filter comprises a channel which encloses the radiation path and which comprises an inner wall on which the reflecting surface is provided.

9. The device as claimed in claim 8, wherein the channel comprises a bend situated between the radiation source and the radiation exit opening.

10. The device as claimed in claim 7, wherein the reflecting surface is provided on a wall which is in thermal contact with a cooling system.

11. The device as claimed in claim 10, wherein the cooling system comprises a circuit filled with a cooling fluid, the wall being in thermal contact with said circuit.

12. The device as claimed in claim 10, wherein the cooling system comprises a fan for generating a gas stream and a guide for guiding said gas stream along the wall.

13. The device as claimed in claim 7, wherein the device is a device for removing hairs from human skin, wherein the radiation source is a flash lamp.

* * * * *